(12) United States Patent
Massimiani

(10) Patent No.: US 11,116,654 B2
(45) Date of Patent: Sep. 14, 2021

(54) DEVICE AND METHOD FOR REINFORCING THE LOWER BODY DURING THE PERFORMANCE OF A COMPOUND WEIGHTLIFTING EXERCISE

(71) Applicant: Stand Strong Company LLC, Pittsburgh, PA (US)

(72) Inventor: Dominic J. Massimiani, Pittsburgh, PA (US)

(73) Assignee: Stand Strong Company LLC, Pittsburgh, PA (US)

( * ) Notice: Subject to any disclaimer, the term of this patent is extended or adjusted under 35 U.S.C. 154(b) by 92 days.

(21) Appl. No.: 16/279,068

(22) Filed: Feb. 19, 2019

(65) Prior Publication Data

US 2019/0262161 A1    Aug. 29, 2019

Related U.S. Application Data

(60) Provisional application No. 62/635,185, filed on Feb. 26, 2018.

(51) Int. Cl.
*A63B 21/00* (2006.01)
*A61F 5/02* (2006.01)

(52) U.S. Cl.
CPC .......... *A61F 5/028* (2013.01); *A63B 21/4009* (2015.10); *A63B 21/4011* (2015.10)

(58) Field of Classification Search
CPC . A61F 5/028; A63B 21/4011; A63B 21/4009; A63B 2209/00; A63B 2225/09; A63B 2209/10; A63B 21/0552; A63B 21/0557; A63B 21/1449; A63B 21/02; A63B 21/1419; A63B 21/1423; A63B 2244/09; A63B 21/4001; A63B 21/4023; A63B 21/4025; A41D 13/0543; A41D 1/067; A41D 13/0015; A41C 3/08
See application file for complete search history.

(56) References Cited

U.S. PATENT DOCUMENTS

| | | | |
|---|---|---|---|
| 5,465,428 A * | 11/1995 | Earl | A63B 21/0552 2/227 |
| 7,559,093 B2 * | 7/2009 | Sudo | A63B 21/4001 2/69 |
| 8,771,155 B1 | 7/2014 | Bell | |
| 9,265,983 B1 | 2/2016 | Bell | |
| 9,498,692 B2 * | 11/2016 | Bledsoe | A63B 69/0059 |
| 10,638,798 B2 * | 5/2020 | Glaude | A41F 9/025 |
| 10,842,204 B2 * | 11/2020 | Stricker | A41D 31/185 |
| 2004/0116260 A1 | 6/2004 | Drennan | |
| 2015/0196789 A1 | 7/2015 | Whitt | |
| 2018/0333604 A1 * | 11/2018 | Thompson | A63B 21/4009 |
| 2019/0380904 A1 * | 12/2019 | Panizzolo | A61H 3/00 |

* cited by examiner

*Primary Examiner* — Jennifer Robertson
*Assistant Examiner* — Catrina A Letterman
(74) *Attorney, Agent, or Firm* — The Webb Law Firm

(57) ABSTRACT

Provided herein is a device for reinforcing the lower body during the performance of a compound weightlifting exercise including at least two thigh bands, each defining an opening for a wearer's thigh, at least two biasing straps, each biasing strap having a proximal end and a distal end, each biasing strap connected at the distal end thereof to one of the at least two generally circular thigh bands, and a waist portion connected to the proximal end of each biasing strap. When worn, each of the biasing straps extends between the waist portion and the thigh bands, over one of the wearer's buttocks and a rear portion of the wearer's thigh.

15 Claims, 11 Drawing Sheets

DEVICE AND METHOD FOR REINFORCING THE LOWER BODY DURING THE PERFORMANCE OF A COMPOUND WEIGHTLIFTING EXERCISE

CROSS-REFERENCE TO RELATED APPLICATIONS

The present application claims priority to U.S. Provisional Patent Application No. 62/635,185, filed Feb. 26, 2018, the content of which is incorporated herein by reference in its entirety.

BACKGROUND OF THE INVENTION

Field of the Invention

The invention relates generally to an exercise device and, more specifically, to a device for reinforcing a user's lower body muscles during the performance of a compound weightlifting exercise.

Description of Related Art

In strength training, there are a number of compound, full body or lower body focused exercises which are considered to be important for increasing the strength and size of the legs and developing core strength. For example, a squat is a compound, full body exercise that trains primarily the muscles of the thighs, hips and buttocks, quadriceps femoris muscles (vastus lateralis, vastus medialis, vastus intermedius, and rectus femoris), hamstrings, and also strengthens the bones, ligaments, and insertion of the tendons throughout the lower body.

Squats in particular are considered a vital exercise for increasing the strength and size of the legs as well as developing core strength. In addition to exercising the lower body, squats utilize muscles of the lower back, upper back, abdominal region, trunk, costal muscles, shoulders, and arms in at least an isometric fashion and thus these muscle groups may also be trained when squatting with proper form.

Although the squat is recognized as one of the best exercises for building muscle and strength, injuries may result, particularly if improper form is used. Further, during the performance of a squat, the smallest muscles involved are often the first to fatigue and may limit the benefits obtained by large muscles. In addition, even the larger muscles of the lower body may fatigue prior to certain core and upper body muscles that are primarily used isometrically during the performance of a squat. Further, such compound exercises that focus mainly on the lower body and core, but which also utilize other parts of the body, include deadlifts and leg presses, and users may experience similar issues during the execution of such compound exercises.

Accordingly, the inventor has recognized a need in the art for a device for reinforcing a user's lower body during the performance of a compound weightlifting exercise.

SUMMARY OF THE INVENTION

Accordingly, it is an object of the invention to provide a device and method for reinforcing the lower body during the performance of a compound weightlifting exercise.

In one non-limiting embodiment, a device for reinforcing the lower body during the performance of a compound weightlifting exercise comprises: a waistband defining an upper opening for a wearer's waist; at least one thigh band defining a lower opening for the wearer's thigh; at least one biasing strap connected to the waistband and the at least one thigh band, wherein, when worn, each of the at least one biasing strap extends over one of the wearer's buttock and a rear upper portion of the wearer's thigh to a rear connection point of the at least one thigh band.

At least one of the waistband and the at least one thigh band may be configured to be releasably secured by a closure on the anterior side of the user when worn. When worn in at least one of a stressed state and an unstressed state, the at least one thigh band may be positioned around one of the user's thighs approximately 50% to 100%, more preferably 60% to 80%, and still more preferably, about 75% of the distance from the top of the knee to the groin. The at least one thigh band may be formed of a material having a lower linear elasticity than the material forming the at least one biasing strap. The waistband and/or at least one thigh band may be formed of a material that stretches linearly by no more than 15%, preferably no more than 10%, and more preferably no more than 5% of its non-stressed length when exposed to 50 pounds of tension. The at least one biasing strap may be formed of a material that stretches linearly by approximately 15% to 85%, more preferably 25% to 75%, more preferably, 35% to 65%, more preferably, 45% to 55%, or still more preferably, by about 50% of its non-stressed length when exposed to 50 pounds of tension. The device may comprise at least two biasing straps, each of the at least two biasing straps having a respective connection point on the posterior portion of the waistband, the respective connection points being separated by an intervening space, wherein each of the at least two biasing straps arranged such that it is substantially perpendicular to the waistband when the device is in an unstressed state.

In a further non-limiting embodiment, a method of reinforcing a user's lower body during the performance of a compound weightlifting exercise, may comprise: providing a waistband surrounding the user's waist; providing at least one thigh band surrounding one of the user's thighs above the knee; and providing at least one biasing strap connected to a posterior portion of the waistband and a posterior portion of the at least one thigh band such that each of the at least one biasing strap extends over one of the wearer's buttock and a rear upper portion of the wearer's thigh.

When the user is in an extended position of the compound weightlifting exercise wherein the user's legs are approximately straight, the at least one biasing strap may be in a first, unstressed state. As the user bends the user's knees during the performance of the compound weightlifting exercise, the waistband and the at least one thigh band may exert tension on the at least one biasing strap, causing the at least one biasing strap to stretch over the wearer's buttock and/or a rear portion of the wearer's thigh such that a biasing force is exerted on the user which urges the user back toward the extended position. The at least one thigh band may be provided approximately 50% to 100%, more preferably 60% to 80%, and still more preferably about 75% of the distance from the top of the knee to the groin, when the device is in at least one of a stressed state and an unstressed state. The waistband and/or the at least one thigh band may be formed of a material having a lower linear elasticity than the material forming the at least one biasing strap. The waistband and/or at least one thigh band may be formed of a material that stretches linearly by no more than 15%, preferably no more than 10%, and more preferably no more than 5% of its non-stressed length when exposed to 50 pounds of tension. The at least one biasing strap may be formed of a material that stretches linearly by approximately 15% to 85%, more preferably 25% to 75%, more preferably, 35% to 65%, more preferably, 45% to 55%, or still more preferably, by about 50% of its non-stressed length when exposed to 50 pounds of tension.

Further embodiments are set forth in the following clauses:

Clause 1: A device for reinforcing the lower body during the performance of a compound weightlifting exercise, comprising: at least two thigh bands, each defining an opening for a wearer's thigh; at least two biasing straps, each biasing strap having a proximal end and a distal end, each biasing strap connected at the distal end thereof to one of the at least two thigh bands; and a waist portion connected to the proximal end of each biasing strap, wherein, when worn, each of the biasing straps extends between the waist portion and the thigh bands, over one of the wearer's buttocks and a rear portion of the wearer's thigh.

Clause 2: The device of clause 1, wherein the waist portion is a waistband configured to be secured to a wearer's waist.

Clause 3: The device of clause 1 or clause 2, wherein at least one of the waistband and the at least two thigh bands is configured to be releasably secured by a closure when worn.

Clause 4: The device of any of clauses 1-3, wherein, when worn, the at least two thigh bands are positioned around each of the wearer's thighs approximately 25% of the distance from the top of a knee to a groin of the wearer.

Clause 5: The device of any of clauses 1-4, wherein, the waistband and the thigh bands are formed of a material having a lower linear elasticity than the material forming the at least one biasing strap.

Clause 6: The device of any of clauses 1-5, wherein the waistband and the thigh bands are formed of a material that stretches linearly by no more than 15% when exposed to 50 pounds of tension.

Clause 7: The device of any of clauses 1-6, wherein the at least two biasing straps are formed of a material that stretches linearly by approximately 75% of its non-stressed length when exposed to 50 pounds of tension.

Clause 8: The device of clause 1, wherein the waist portion comprises a loop configured to permit a weight belt to pass therethrough.

Clause 9: The device of clause 8, wherein, when worn, the at least two thigh bands are positioned around each of the wearer's thighs approximately 25% of the distance from the top of a knee to a groin of the wearer.

Clause 10: The device of clause 8 or clause 9, wherein the thigh bands are formed of a material that stretches linearly by approximately 50-75% when exposed to 50 pounds of tension.

Clause 11: The device of any of clauses 8-10, wherein the at least two biasing straps are formed of a material that stretches linearly by approximately 50-75% of its non-stressed length when exposed to 50 pounds of tension.

Clause 12: A method of reinforcing a wearer's lower body during the performance of a compound weightlifting exercise, comprising: positioning the device of any of clauses 1-11 on a wearer, such that: the at least two thigh bands are positioned around each of the wearer's thighs; the waist portion is positioned at the wearer's waist; and the at least two biasing straps extend over the wearer's buttocks and a rear portion of the wearer's thigh.

Clause 13: The method of clause 12, wherein the at least two thigh bands are positioned approximately 25% of the distance from the top of a knee to a groin of the wearer.

Clause 14: The method of clause 12 or clause 13, wherein, when the wearer is in an extended position of the compound weightlifting exercise wherein the wearer's legs are approximately straight, the at least two biasing straps are in a first, unstressed state.

Clause 15: The method of any of clauses 12-14, wherein, as the wearer bends the wearer's knees during performance of the compound weightlifting exercise, the waist portion and the thigh bands exert tension on the at least two biasing straps, causing the at least two biasing straps to stretch over the wearer's buttocks and a rear portion of the wearer's thighs such that a biasing force is exerted on the wearer, which urges the wearer back toward the extended position.

Clause 16: The method of any of clauses 12-15, wherein the thigh bands are formed of a material that stretches linearly by approximately 50-75% when exposed to 50 pounds of tension.

Clause 17: The method of any of clauses 12-16, wherein the at least two biasing straps are formed of a material that stretches linearly by approximately 50-75% of its non-stressed length when exposed to 50 pounds of tension.

Clause 18: The method of any of clauses 12-17, wherein the compound weightlifting exercise is selected from the group consisting of barbell squat, barbell front squat, body-weight squat, conventional deadlift, sumo deadlift, Romanian deadlift, and leg press.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Figure 1:
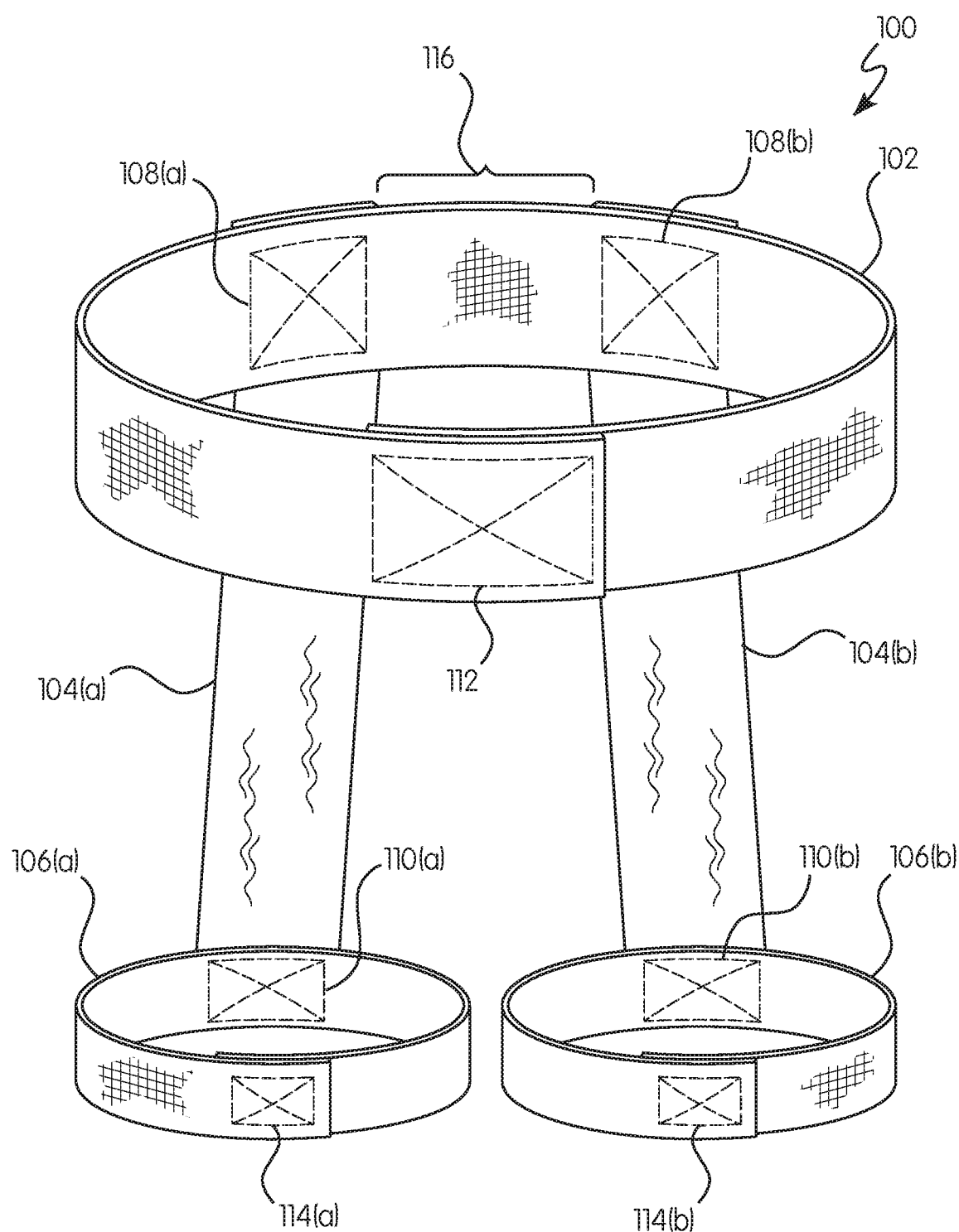
FIG. 1 is a front perspective view of a device for reinforcing the lower body during a compound weightlifting exercise in accordance with a non-limiting embodiment of the present invention.

For purposes of the description herein, the terms "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary configurations of the invention. Hence, specific dimensions and other physical characteristics related to the configurations disclosed herein are not to be considered as limiting.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, the terms "wearer" and "user" mean an individual who utilizes the device described herein, and the terms are used interchangeably.

As used in the specification and the claims, the singular form of "a", "an", and "the" include plural referents unless the context clearly dictates otherwise.

As used herein, the terms "first," "second," "third," and the like are not intended to refer to any particular order or chronology, but instead refer to two different conditions or properties, except where the context clearly dictates otherwise.

Other than where explicitly indicated, all numbers expressing quantities of ingredients, reaction conditions, and so forth used in the specification and claims are to be understood as modified in all instances by the term "about."

As used herein, the terms "about" or "approximately" mean the stated value or range, plus or minus 10%.

Figure 2:
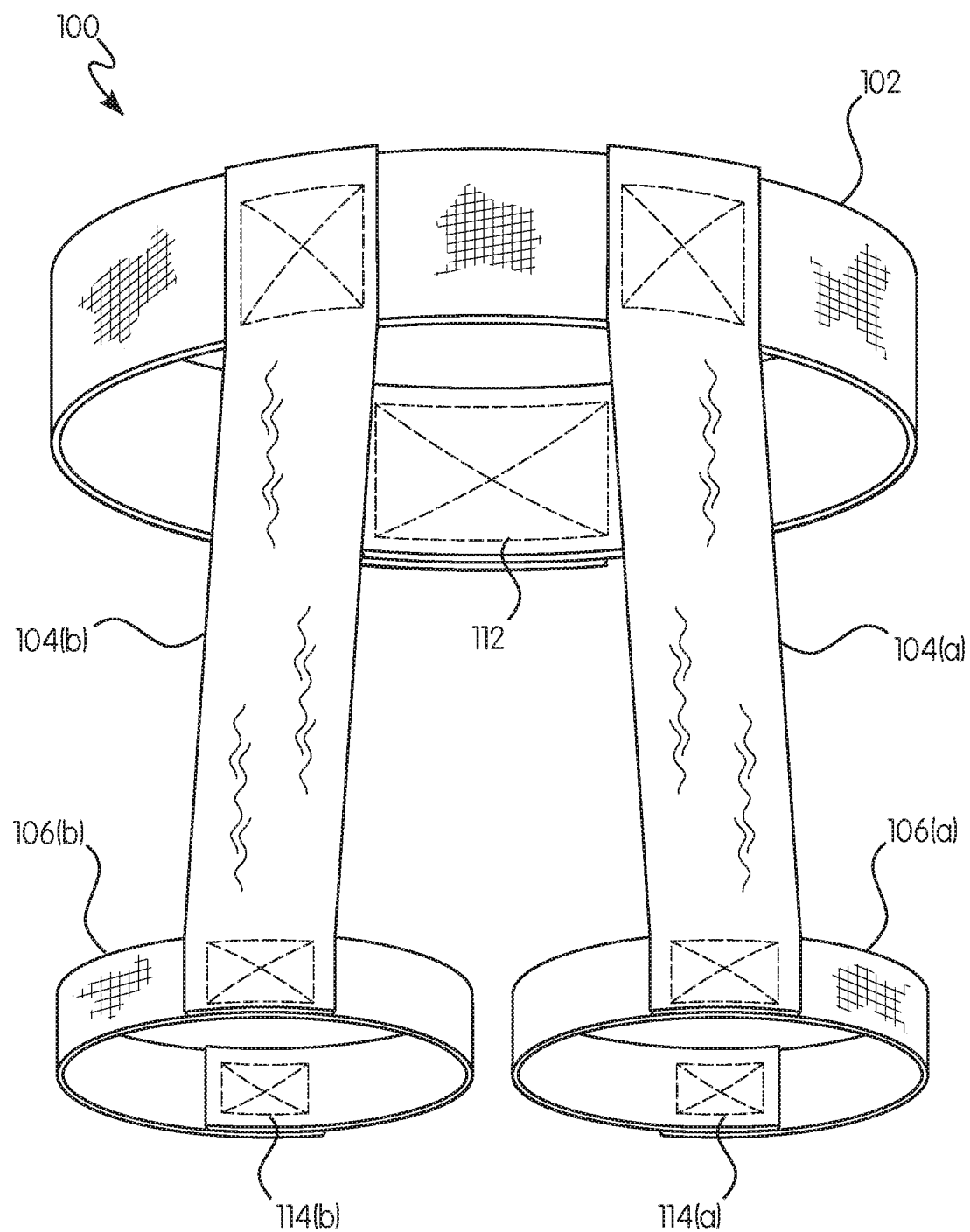
FIG. 2 is a rear perspective view of the device shown in FIG. 1.

Referring now to FIGS. 1 and 2, FIG. 1 shows a front perspective view of a device 100 for reinforcing the lower body during a compound weightlifting exercise in accordance with a non-limiting embodiment of the invention, and FIG. 2 shows a rear perspective view of the device 100 shown in FIG. 1.

In the non-limiting embodiment shown, a waistband 102 is configured to fit around a user's waist and to be releasably secured in front of the user when worn by way of a waistband closure 112. The waistband 102 is provided with two biasing straps 104(a, b), the upper ends of which are attached to a posterior portion of the waistband 102 at waistband connection points 108(a, b). In the non-limiting embodiment shown, the waistband connection points 108(a, b) are separated by an intervening space 116.

The lower end of each biasing strap 104(a, b) is attached to a posterior portion of a respective thigh band 106(a, b) at a thigh band connection point 110(a, b), with the respective thigh band connection points 110(a, b) falling approximately in the middle of the back of the thigh when the device 100 is worn. Each thigh band 106(a, b) is configured to fit around a user's thigh and to be releasably secured thereto by a thigh band closure 114 (a, b).

Figure 3:
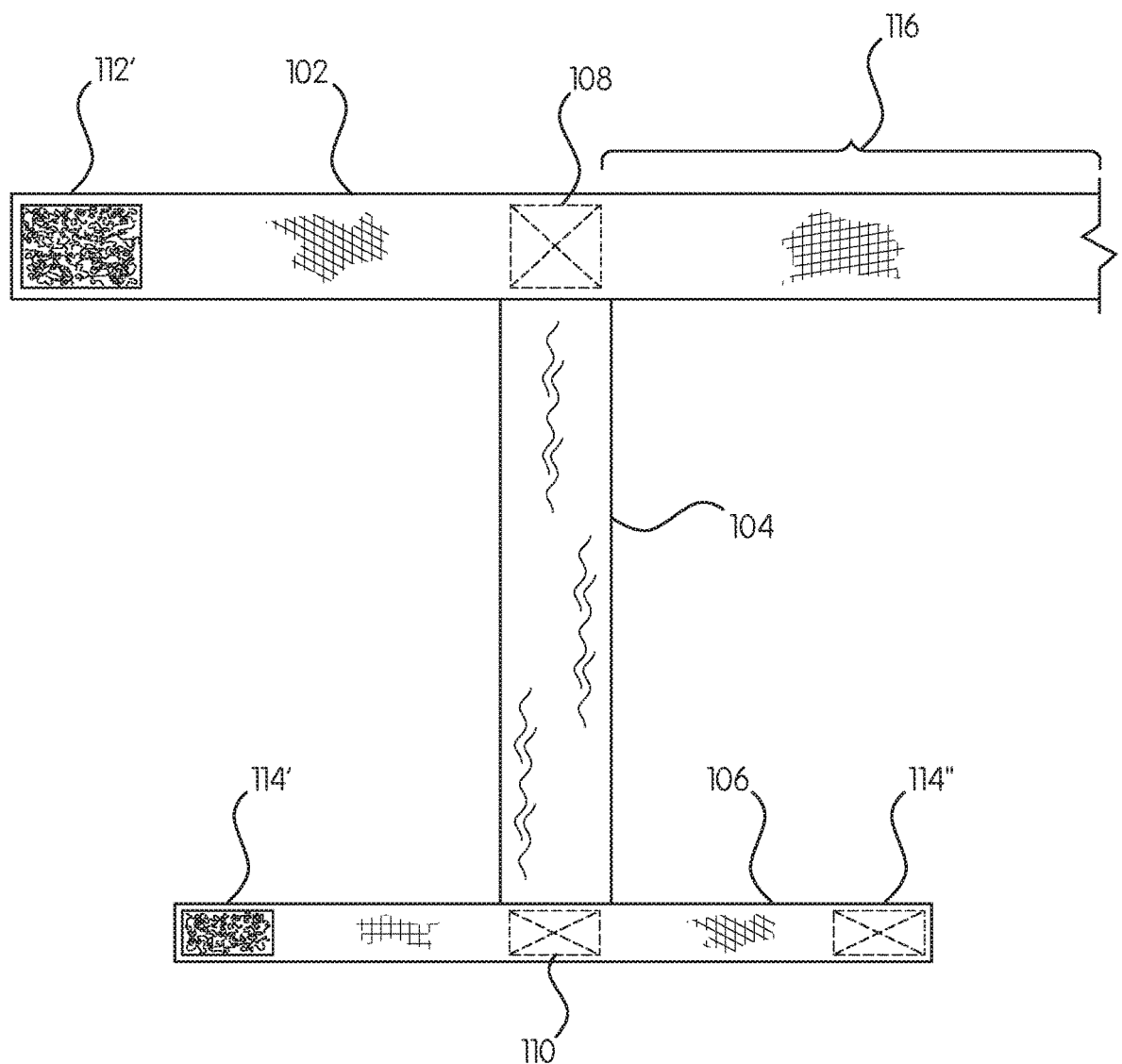
FIG. 3 is a cut-away view showing a portion of a waistband, a biasing strap, and a thigh band in an unfolded configuration in accordance with a non-limiting embodiment of the present invention.

Referring now to FIG. 3, FIG. 3 is a cut-away view of a right portion of the device 100 showing a right portion of the waistband 102, a right biasing strap 104(a), and a right thigh band 106(a) in an unfolded configuration in accordance with a non-limiting embodiment of the present invention. Visible FIG. 3 are a top portion 112' of waistband closure 112 and both a top portion 114' and a bottom portion 114" of thigh band 106. In non-limiting embodiments, the left portion of weightlifting support device 100 may substantially mirror the right portion shown in FIG. 3, albeit having a bottom portion (not shown) configured to connect to the top portion 112' of closure 112.

With reference to FIGS. 1-3, in non-limiting embodiments, the waistband closure 112 and/or the thigh band closures 114(a, b) may take the form of various releasable fasteners, such as a pair of hook and loop fasteners (e.g., Velcro®), a male and female end of a buckle, one or more adhesive strips, or the like. It will be appreciated that various configurations are possible in accordance with the present invention.

Further, it is to be appreciated that in some non-limiting embodiments, any of waistband closure 112 and thigh band closures 114(a, b) may be absent. For example, in one non-limiting embodiment, any of waistband 102 and thigh bands 106 may be a continuous loop formed from an elastic material such that they may be slid over the waist and/or thighs, respectively, and held in place via elastic forces and friction. Further, in another exemplary embodiment, waistband 102 or thigh bands 106 may be provided with a ratchet mechanism, a cinch, a tightening device, or the like, such that the waistband and/or thigh bands may be slid over the user's waist and thighs, respectively, while donning the device and then tightened prior to use. It will be appreciated that various configurations are possible in accordance with the present invention.

In non-limiting embodiments, the waistband connection points 108(a, b) and/or the thigh band connection points 110(a, b) may take the form of various releasable or non-releasable connection mechanisms and/or any of the waistband and/or thigh bands may be formed integrally with the biasing straps. For example, in the non-limiting embodiment shown in FIGS. 1-3, the biasing straps are stitched onto the outside portion of the waistband 102 at waistband connection points 108(a, b) and to the respective thigh bands at thigh band connection points 110(a, b), however, it will be appreciated that a variety of ways of connecting such elements may be utilized in accordance with the present invention.

For example, in one non-limiting embodiment, any of waistband 102 and thigh bands 106(a, b) may be equipped with a plurality of slots or other connecting elements through which a portion of the biasing strap or a connecting element attached thereto may be passed. In such non-limiting embodiments, the waistband 102 may take the form of a lifting belt which increases intra-abdominal pressure while conducting a lift, and the biasing straps 104(a, b) may be detachable such that waistband 102 can also be used as a lifting belt by itself, thus allowing for increased modularity and versatility of the device 100. In such non-limiting examples, the waistband may have multiple slots and/or other connecting elements such that the user could adjust the placement of each of biasing straps 104(a, b) on the waistband and thus adjust the amount of intervening space 116 on the posterior portion of the waistband and the positioning of the biasing straps on the back of the thighs. Further, in non-limiting embodiments, any of the waistband 102 and individual thigh bands 106(a, b) may be equipped with multiple slots and/or other connection points for each leg for the connection of multiple biasing straps thereto. In such non-limiting embodiments, a user may add additional biasing straps to change the resistance that is imparted by the device 100 while performing a compound exercise as described herein.

Figure 4:
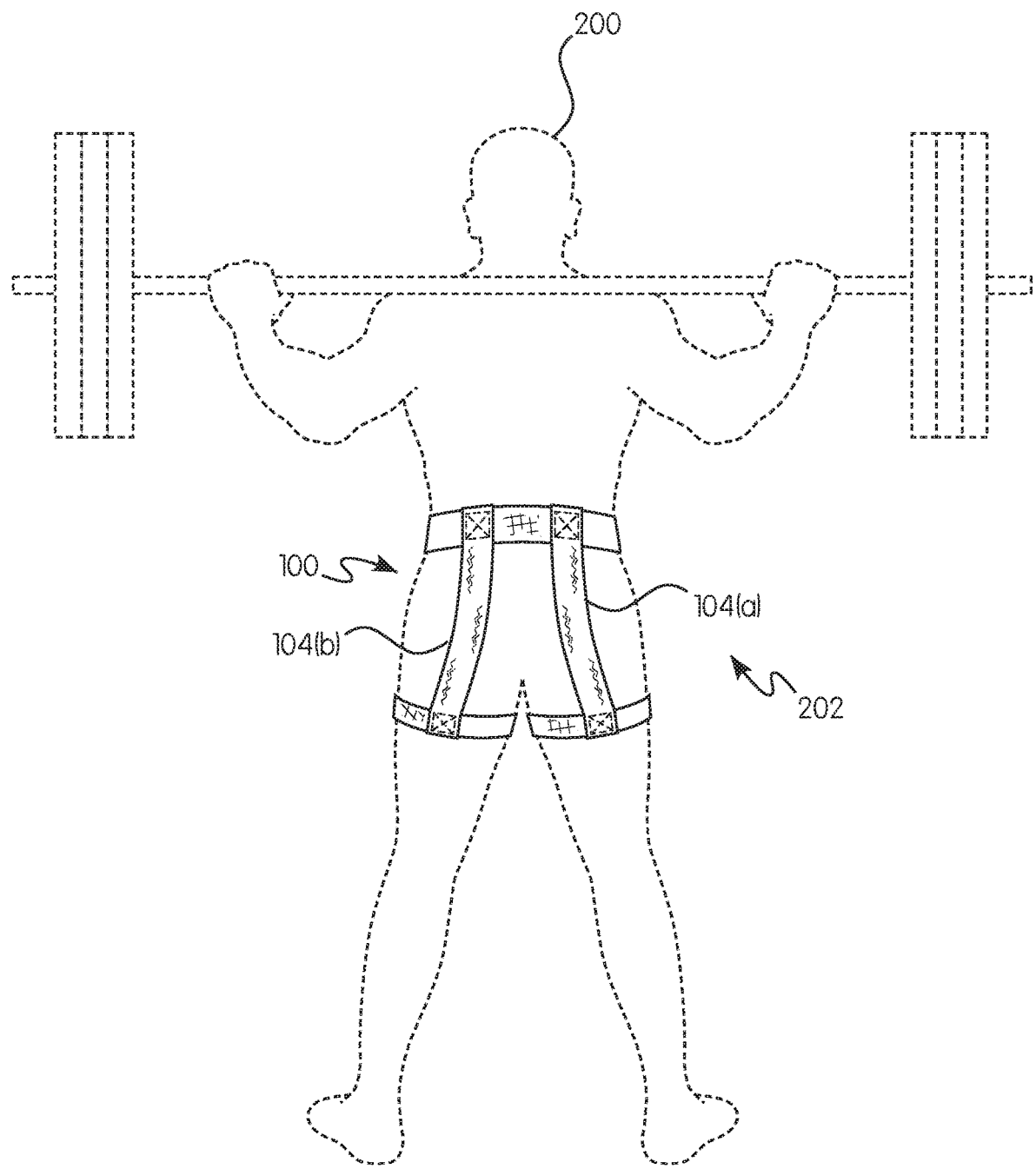
FIG. 4 is a rear perspective view of a user in the top position of a squat exercise while wearing a device for reinforcing the lower body during a compound weightlifting exercise in accordance with a non-limiting embodiment of the present invention.

In non-limiting embodiments, the biasing straps 104 may be attached to the waistband 102 such that they are approximately perpendicular thereto when the device is at rest, and such that each biasing strap extends approximately across the center of one of the buttocks and the back of the respective upper thigh when the device is worn, with the intervening space 116 being approximately ¼ of the distance across the back of the user, from hip to hip (for example, as in the non-limiting embodiment shown in FIG. 4). In non-limiting embodiments, the biasing straps may be of a length such that the thigh bands fall approximately 50% to 100%, more preferably 60% to 80%, and still more preferably about 75% of the way from the top of the knee to the groin when the user is wearing the device in a standing position. In non-limiting embodiments, the biasing straps may be of a length such that the thigh bands fall approximately 15% to 40%, more preferably about 25% of the way from the top of the knee to the groin when the user is wearing the device in a standing position.

With continued reference to FIGS. 1-3 in non-limiting embodiments, the waistband 102 and/or one or both thigh bands 106 may be formed of materials having a relatively low linear elasticity as compared to that of the biasing straps 104 and as further detailed below. In non-limiting examples, the waistband 102 and thigh bands 106 may be made of leather, faux leather, a nylon/polyester webbing (e.g., automobile "seatbelt material"), or various natural or synthetic "non-stretch" fabrics. This may improve the performance of the device 100 by limiting the majority of stretching that occurs during the performance of a compound exercise such as a squat to the biasing straps 104 and thus ensure that the reinforcement caused by the biasing straps is focused in regions of the back portion of the thigh and the buttocks. Further, this may reduce instances of the waistband 102 or the thigh bands 106(a, b) becoming dislodged due to forces from the biasing straps 104 and/or the natural expansion and contraction of the body during the exercise that is performed.

More specifically, in non-limiting embodiments, each of waistband 102 and thigh bands 106 may be formed of a material that stretches by no more than 15%, preferably no more than 10%, and more preferably no more than 5% when exposed to 50 pounds of tension. In a non-limiting embodiment, waistband 102 may be approximately 40 inches in length and may stretch to no more than 46 inches, preferably no more than 44 inches, and more preferably no more than 42 inches when exposed to 50 pounds of tension. Further, in some non-limiting embodiments, waistband 102 and/or thigh bands 106 may be formed of a material that does not stretch to any noticeable extent (e.g., less than 1%) when exposed to 50 pounds of tension. In some non-limiting embodiments, only the waistband is formed of a material that cannot appreciably stretch, and the thigh bands are formed of a material that is more elastic and can stretch, for example, approximately 100%, between approximately 50% and 100%, optionally between approximately 50% and 75%, when exposed to 50 pounds of tension With continued reference to FIGS. 1-3 in non-limiting embodiments each of biasing straps 104(a, b) may be formed of a high-elastic material, for example, such as lycra spandex, neoprene, other elastic fabric materials, polymer or metallic springs (which, in such non-limiting embodiments are preferably provided inside of a covering to reduce instances of pinching), rubber bands or other bands formed from various elastomers, or other materials sufficient to stretch and impart a biasing force on a user wearing device 100 when the user performs a compound exercise as described herein.

In non-limiting embodiments, the biasing straps may be formed such that they stretch approximately 15% to 85%, more preferably 25% to 75%, more preferably, 35% to 65%, more preferably, 45% to 55%, or still more preferably about 50% when exposed to 50 pounds of tension.

For example, in non-limiting embodiments, each biasing strap may be approximately 18 inches long and may stretch to 19 inches (i.e., approximately 5%) under 5 pounds of tension, to 22 inches (i.e., approximately 22%) under 10 pounds of tension, to 26 inches under 25 pounds of tension (i.e., approximately 44%), to 27 inches (i.e., approximately 44%) under 35 pounds of tension, and still to about 27 inches (i.e., approximately 44%) under 50 pounds of tension, such that under normal forces which can be imparted by a human, the biasing strap stretches to up to approximately 50% longer than its initial length. In non-limiting embodiments, each biasing strap may be approximately 10-15 inches long, in some embodiments approximately 12 inches long. In non-limiting embodiments, each biasing strap is approximately 13 inches long, measured from the base of the waistband (or connection point (108a, b) and the base of the thigh band 106(a, b)). In non-limiting embodiments, each biasing strap is approximately 3 inches wide.

In non-limiting embodiments, the biasing forces and stretching characteristics discussed above may be provided by a single biasing strap per leg or may be divided among multiple biasing straps per leg. It will be appreciated that these parameters are only illustrative and that multiple degrees of elasticity of the biasing straps may be utilized in accordance with the present invention. For example, the device including biasing straps having the above-described elastic characteristics has been found to increase the maximum weight most users can carry while successfully completing a squat exercise by about 10%, however, the biasing force imparted may be adjusted in accordance with the present invention by changing the length or elasticity thereof to accommodate the needs of individual users.

According to one non-limiting embodiment of the present invention, the device may comprise 5 bands, as follows:
  The 5 bands include two thigh bands, two vertical bands (serving as biasing straps), and one waistband.

The thigh bands may have the following dimensions: 3" wide, by 28" long (for smaller persons) or 3" wide by 35" long (for larger persons);

The vertical bands may have the following dimensions: 3" wide by 18" long; and

The waistband may have the following dimensions: 4" wide by 38" long (for smaller persons) or 3" wide by 48" long (for larger persons).

On the thigh bands, there may be a 7" strip of "hooks" (e.g., rough Velcro®) on one end and a 3" strip of "loops" (e.g., soft Velcro®) on the opposing end;

On the waistband, there may be a 10" strip of "hooks" (e.g., rough Velcro®) on one end and a 3" strip of "loops" (e.g., soft Velcro®) on the opposing end; and The vertical bands may be sewn onto the waist band, centered on the back of the waistband, and the connection points of the vertical bands on the waistband may be approximately one inch apart.

Figure 5:
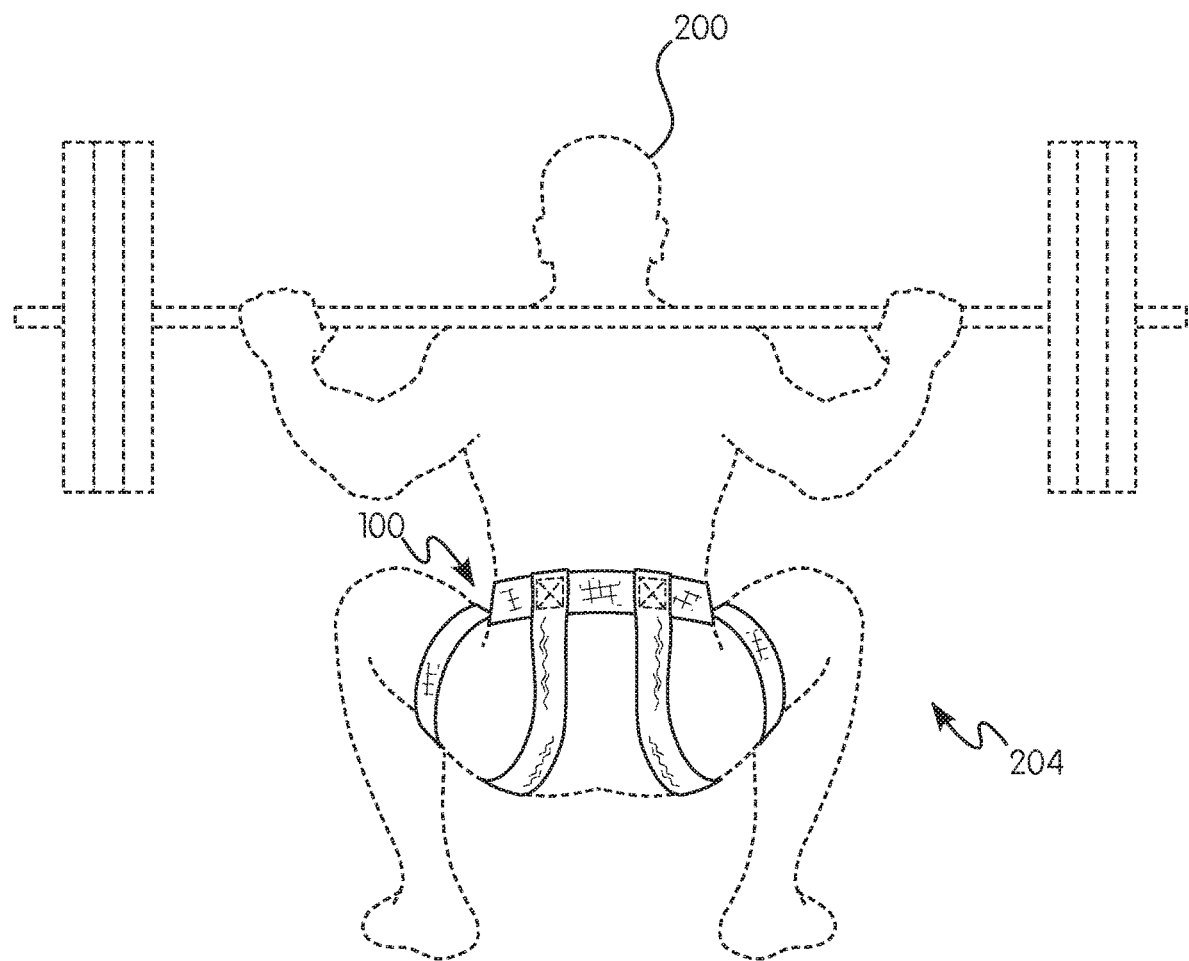
FIG. 5 is a rear perspective view of the user and device shown in FIG. 4 with the user in the bottom position of a squat exercise in accordance with a non-limiting embodiment of the invention.

With reference to FIGS. 4 and 5, FIG. 4 is a rear perspective view of a user 200 in the top position of a squat exercise and wearing device 100 in accordance with a non-limiting embodiment of the present invention, and FIG. 5 is a rear perspective view of the user 200 and device shown in FIG. 4, with the user 200 in the bottom position of a squat exercise in accordance with a non-limiting embodiment of the invention.

In the non-limiting embodiment shown, the device 100 is strapped around a user's waist and thighs such that the biasing straps approximately bisect each respective buttock when user 200 is in the upper position 202 of a squat exercise. With reference to FIG. 5, as the user 200 "sits" into the lower position 204 of a squat exercise, each biasing strap stretches across its respective buttock and rear upper thigh (though, in embodiments as described above and below, the biasing strap stretches across the lower thigh) and imparts a biasing force which urges the user back towards the upper position 202. In this way, the device 100 supplements a user's natural strength and reduces fatigue of the joints (e.g., the knees) and smaller muscles of the lower body. In particular, it is noted that due to the positioning and elastic characteristics of the biasing straps, the biasing forces exerted on the user increase as the user moves toward the lower position 204 of the exercise, which is often where a user experiences the most difficulty in the performance of a squat or similar compound weightlifting exercise, and decreases as the user moves back toward the upper position 202, which is often the least strenuous portion of the exercise. As such, the user may be enabled to perform a squat exercise or other compound exercise with a greater weight or perform more repetitions with the same weight and this may allow the user to strengthen his or her larger muscles by reducing the extent the user is limited by weaknesses in smaller muscles and joints or by the increased difficulty of the exercise near the lower position 204 thereof. Further, this may allow the user to provide further exercise to various muscles that are primarily used in an isometric fashion during a squat exercise or other compound exercise, while reducing the extent to which the user is limited by lower body muscles which move to a greater extent during the exercise (e.g., the quadriceps, hamstrings, and glutes).

Although FIGS. 4 and 5 illustrate the function of a non-limiting embodiment of the invention during a squat exercise, it is noted that non-limiting embodiments of the present invention may also be utilized in a similar way for other compound exercises that focus at least partially on the lower body, for example and without limitation, a barbell squat, barbell front squat, body-weight squat, conventional deadlift, sumo deadlift, Romanian deadlift, or leg press. In a similar way as described with reference to FIGS. 4 and 5 above, in non-limiting embodiments the biasing straps exert a force on the user during a deadlift, leg press, or other similar compound exercise that urges the user from a "seated" position towards an "extended" position and thus may assist the user in performing the respective compound exercise and may reduce the disadvantages associated with the stresses they impart on the weaker muscles and joints or allow further working of muscles that work primarily isometrically during the exercise, as discussed above.

Although FIGS. 1-5 show non-limiting embodiments of the weightlifting support device 100 having a pair of biasing straps and thigh straps which accommodate both legs of most users, in accordance with further non-limiting embodiments of the present invention, it is also contemplated that only one biasing strap and thigh band may be provided. Such non-limiting embodiments may serve to aid users who have a disability, weakness, or injury in one leg and who may benefit by having added support added to the "bad leg" so to allow the user's other leg to undertake increased exercise by reducing the extent to which the "bad leg" inhibits the user's overall performance.

In further non-limiting embodiments, for users where one leg may be missing and who may be using a prosthetic to perform a compound lower body exercise as describe herein, a non-limiting embodiment of the invention may include only a single biasing strap and a modified thigh band which may be fitted to a portion of a prosthetic and/or residual limb, in order to compensate for a reduction in strength which may be associated with the lack of a natural limb present on that side of the body and thus reduce the extent to which the performance of the other leg may be limited by this reduction in strength.

Figure 6:
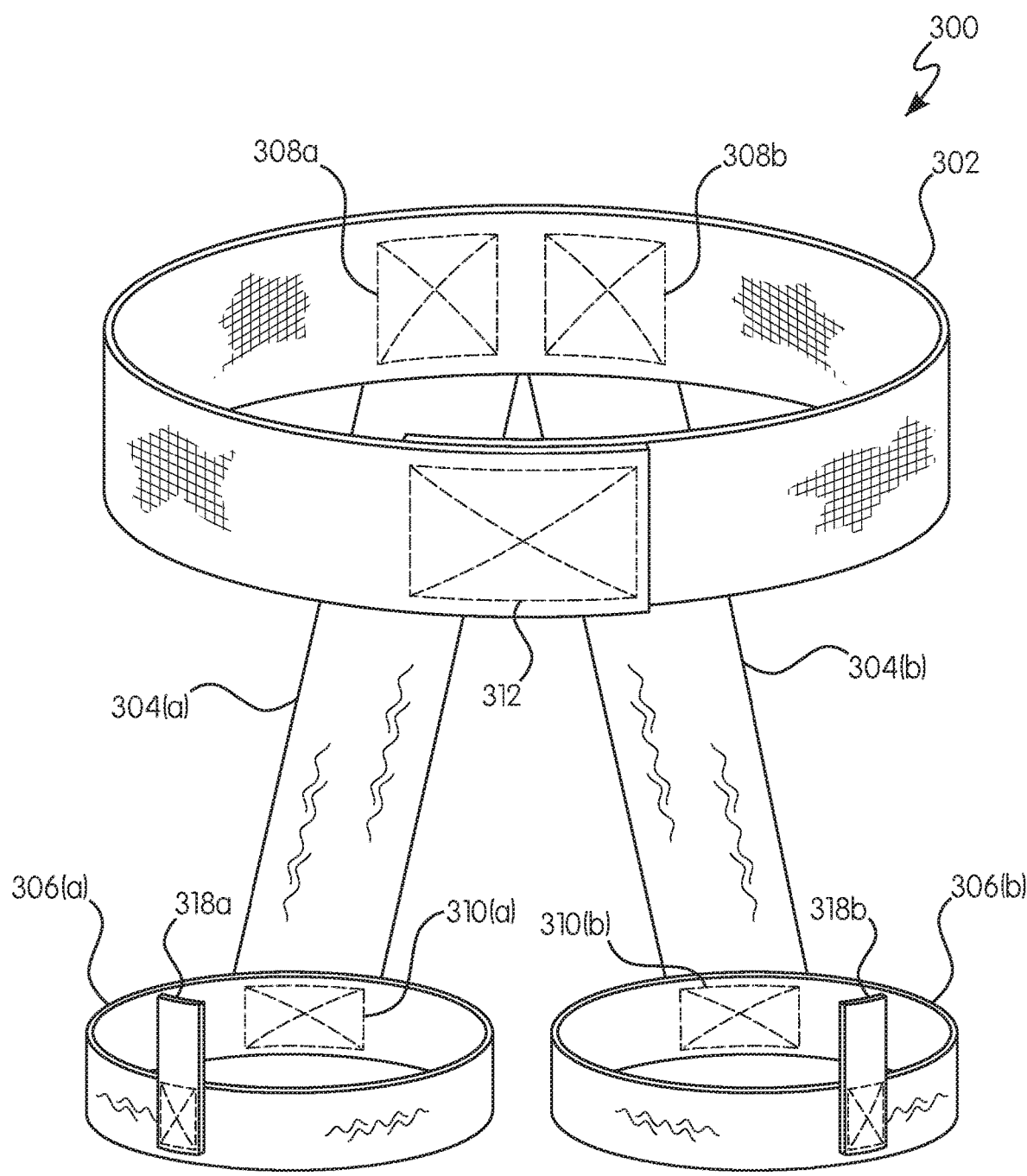
FIG. 6 is a front perspective view of a device for reinforcing the lower body during a compound weightlifting exercise in accordance with a non-limiting embodiment of the present invention.
Figure 7:
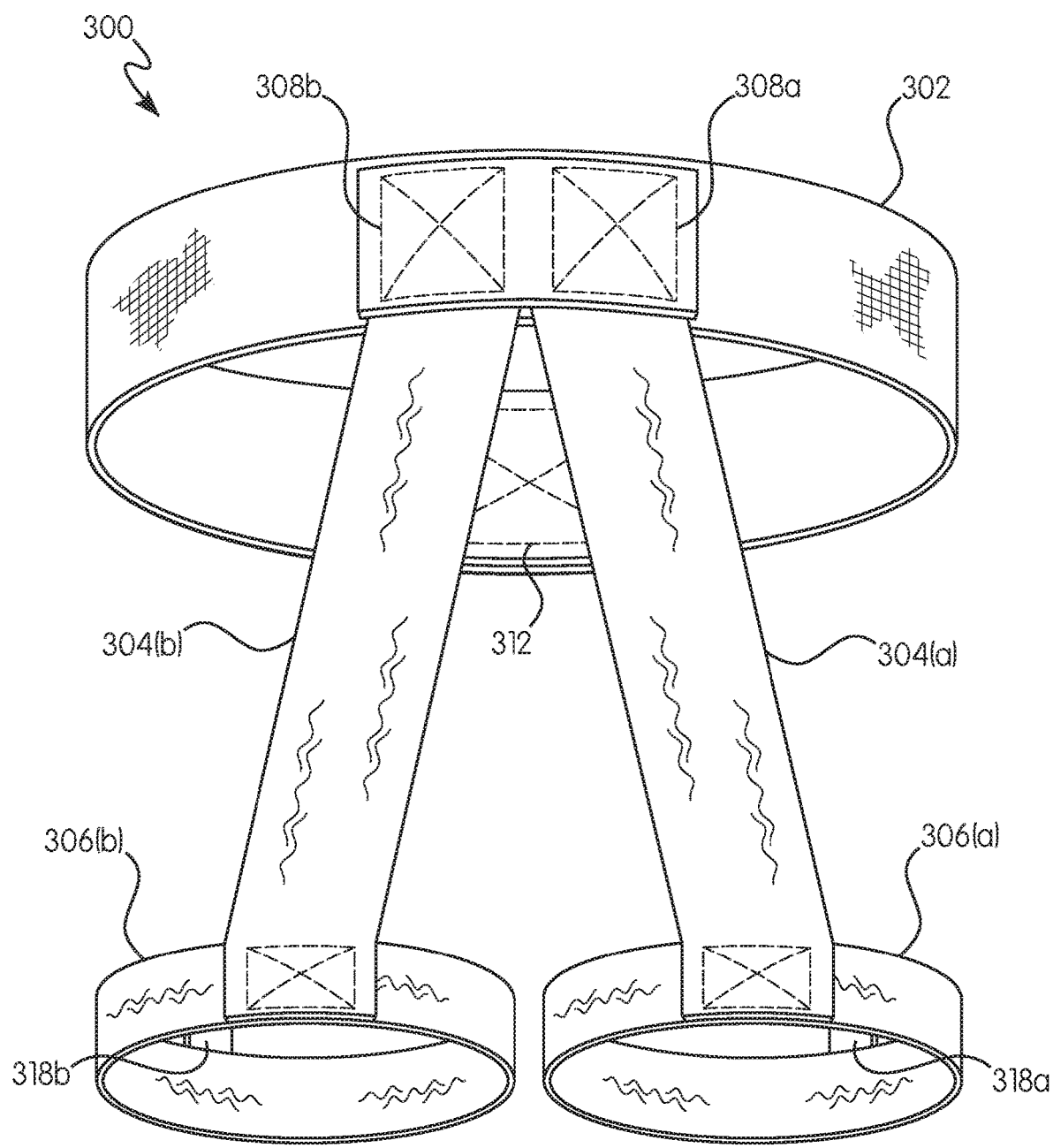
FIG. 7 is a rear perspective view of the device shown in FIG. 6.

Referring now to FIGS. 6 and 7, FIG. 6 shows a front perspective view of a device 300 for reinforcing the lower body during a compound weightlifting exercise in accordance with a non-limiting embodiment of the invention, and FIG. 7 shows a rear perspective view of the device 300 shown in FIG. 6.

In the non-limiting embodiment shown, a waistband 302 is configured to fit around a user's waist and to be releasably secured in front of the user when worn by way of a waistband closure 312. The waistband 302 is provided with two biasing straps 304(a, b), the upper ends of which are attached to a posterior portion of the waistband 302 at waistband connection points 308(a, b). In non-limiting embodiments, biasing straps 304(a, b) are of a fixed length (e.g., they are not adjusted based on the height of the individual user). In non-limiting embodiments, biasing straps 304(a, b) are of a fixed width (e.g., they are not adjusted based on any aspect of the individual user). In the non-limiting embodiment shown, the waistband connection points 308(a, b) are not substantially separated (as compared to the non-limiting embodiment of FIGS. 1 and 2), such that the connection points can be considered to be the same connection point.

The lower end of each biasing strap 304(a, b) is attached to a posterior portion of a respective thigh band 306(a, b) at a thigh band connection point 310(a, b), with the respective thigh band connection points 310(a, b) falling approximately in the middle of the back of the thigh when the device 300 is worn. Each thigh band 306(a, b) is configured to fit around a user's thigh. In non-limiting embodiments, the thigh bands 306(a, b) are positioned lower on a user's leg than the middle of the thigh. In non-limiting embodiments, the thigh bands 306(a, b) are positioned halfway between the middle of a user's thigh and the user's knee. In the non-limiting embodiment shown in FIGS. 6 and 7, unlike that shown in FIGS. 1 and 2, there is no thigh band closure. Rather, in the non-limiting embodiment shown in FIGS. 6 and 7, the thigh bands 306(*a, b*) are continuous loops formed from an elastic material such that they may be slid over the thighs and held in place via elastic forces and friction. In non-limiting embodiments, as described above, to enable the thigh bands to accommodate a range of potential users, the thigh bands are formed of a material that stretches by approximately 100%, between approximately 50% and 100%, optionally between approximately 50% and 75% when exposed to 50 pounds of tension. As described above with regard to the non-limiting embodiment of FIGS. 1 and 2, it will be appreciated that various configurations are possible in accordance with the present invention.

Further to the above, and with continuing reference to FIGS. 6 and 7, the non-limiting embodiment shown therein includes tabs 318(*a, b*) to aid a user in sliding the thigh bands 306(*a, b*) onto their thighs. Tabs 318(*a, b*) may be removably secured to thigh bands 306(*a, b*), or, in non-limiting embodiments, may be formed integrally with the thigh bands 306(*a, b*), to increase the pressure that can be applied to pull the thigh bands 306(*a, b*) onto a user's thigh without risking detachment of the tabs therefrom.

In non-limiting embodiments, the waistband connection points 308(*a, b*) and/or the thigh band connection points 310(*a, b*) may take the form of various releasable or non-releasable connection mechanisms and/or any of the waistband and/or thigh bands may be formed integrally with the biasing straps. For example, in the non-limiting embodiment shown in FIGS. 6 and 7, the biasing straps are stitched onto the outside portion of the waistband 302 at waistband connection points 308(*a, b*) and to the respective thigh bands at thigh band connection points 310(*a, b*), however, as described above, it will be appreciated that a variety of ways of connecting such elements may be utilized in accordance with the present invention.

With continuing reference to FIGS. 6 and 7, in non-limiting embodiments each of biasing straps 304(*a, b*) may be formed of an elastic material, for example, such as lycra spandex, neoprene, other elastic fabric materials, polymer or metallic springs (which, in such non-limiting embodiments are preferably provided inside of a covering to reduce instances of pinching), rubber bands or other bands formed from various elastomers, or other materials sufficient to stretch and impart a biasing force on a user wearing device 300 when the user performs a compound exercise as described herein. In non-limiting embodiments, biasing straps 304(*a, b*) are formed of a combination of polyester and natural rubber in different yarn and rubber strengths.

In non-limiting embodiments, the biasing straps 304(*a, b*) are formed of a woven elastic including a combination of a spun polyester, a textured polyester, and a natural latex. In non-limiting embodiments, the biasing straps are formed of a woven elastic that has the following characteristics:

| | |
|---|---|
| Warp Yarn | 2/150 textured polyester |
| Binder Yarn | 2/150 textured polyester |
| Weft Yarn | 2/150 textured polyester |
| Elongation | 55% ± 10% |
| Elastomer | Natural latex rubber |

In non-limiting embodiments, the biasing straps are formed of a woven elastic that has the following characteristics:

| | |
|---|---|
| Warp Yarn | Spun polyester |
| Weft Yarn | Textured polyester |
| Elongation | 120% ± 10% |
| Elastomer | Natural latex rubber |

In non-limiting embodiments, each biasing strap may be approximately 10-15 inches long, in some embodiments approximately 12 inches long. In non-limiting embodiments, each biasing strap is approximately 13 inches long, measured from the base of the waistband (or connection point (308*a, b*) and the base of the thigh band 306(*a, b*)). In non-limiting embodiments, each biasing strap is approximately 3 inches wide.

In non-limiting embodiments, the biasing straps may be formed such that they stretch approximately 15% to 85%, more preferably 25% to 75%, more preferably, 35% to 65%, more preferably, 45% to 55%, or still more preferably about 50% when exposed to 50 pounds of tension. For example, in one non-limiting embodiment, each biasing strap may be approximately 13 inches long and may stretch to 18.5 inches under 10 pounds of tension, to 21 inches under 25 pounds of tension, to 23 inches under 35 pounds of tension, and to 23 inches under 50 pounds of tension, such that under normal forces which can be imparted by a human, the biasing straps stretch to up to approximately 77% longer than its initial length.

Figure 8:
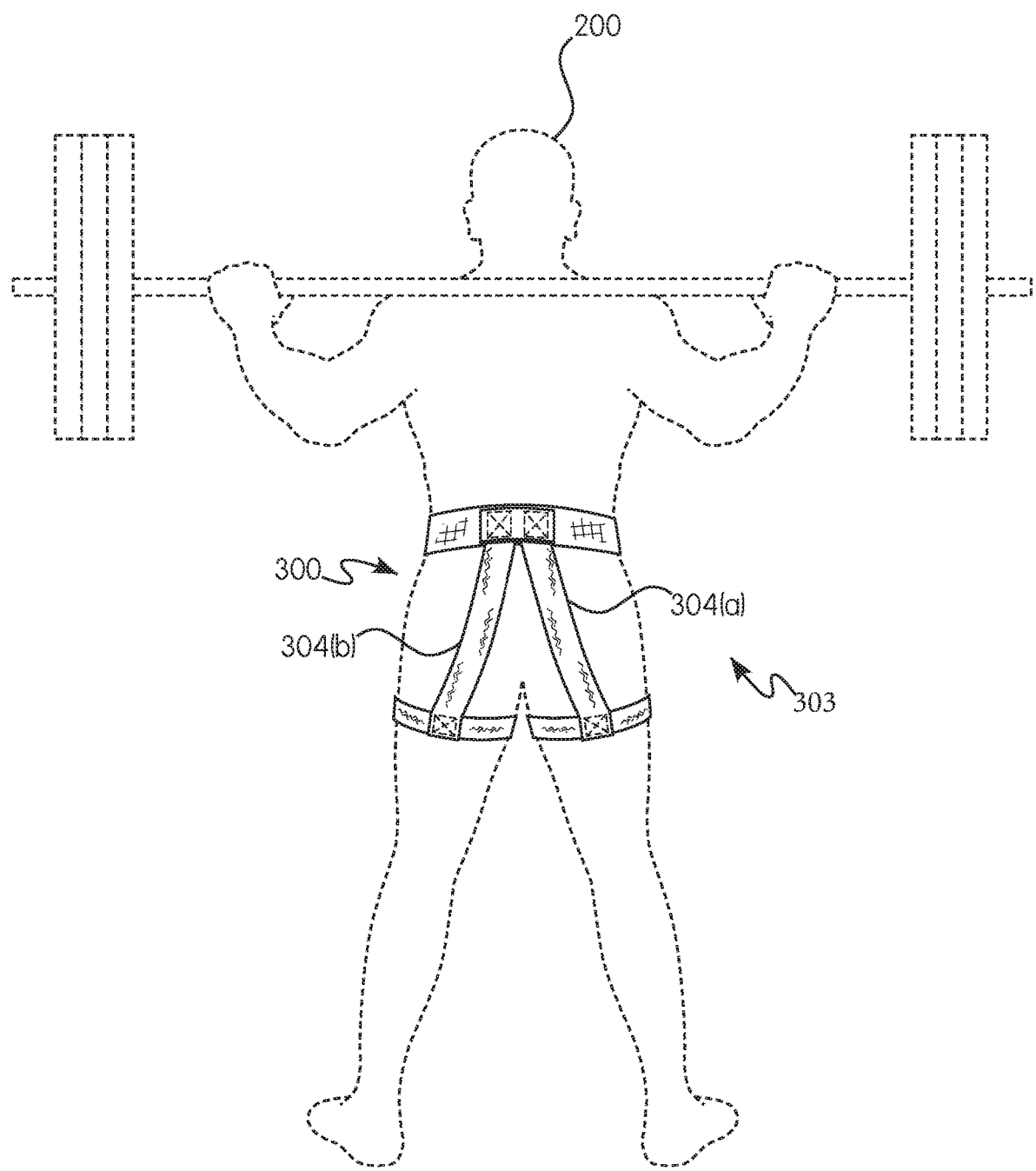
FIG. 8 is a rear perspective view of a user in the top position of a squat exercise while wearing a device for reinforcing the lower body during a compound weightlifting exercise in accordance with a non-limiting embodiment of the present invention.
Figure 9:
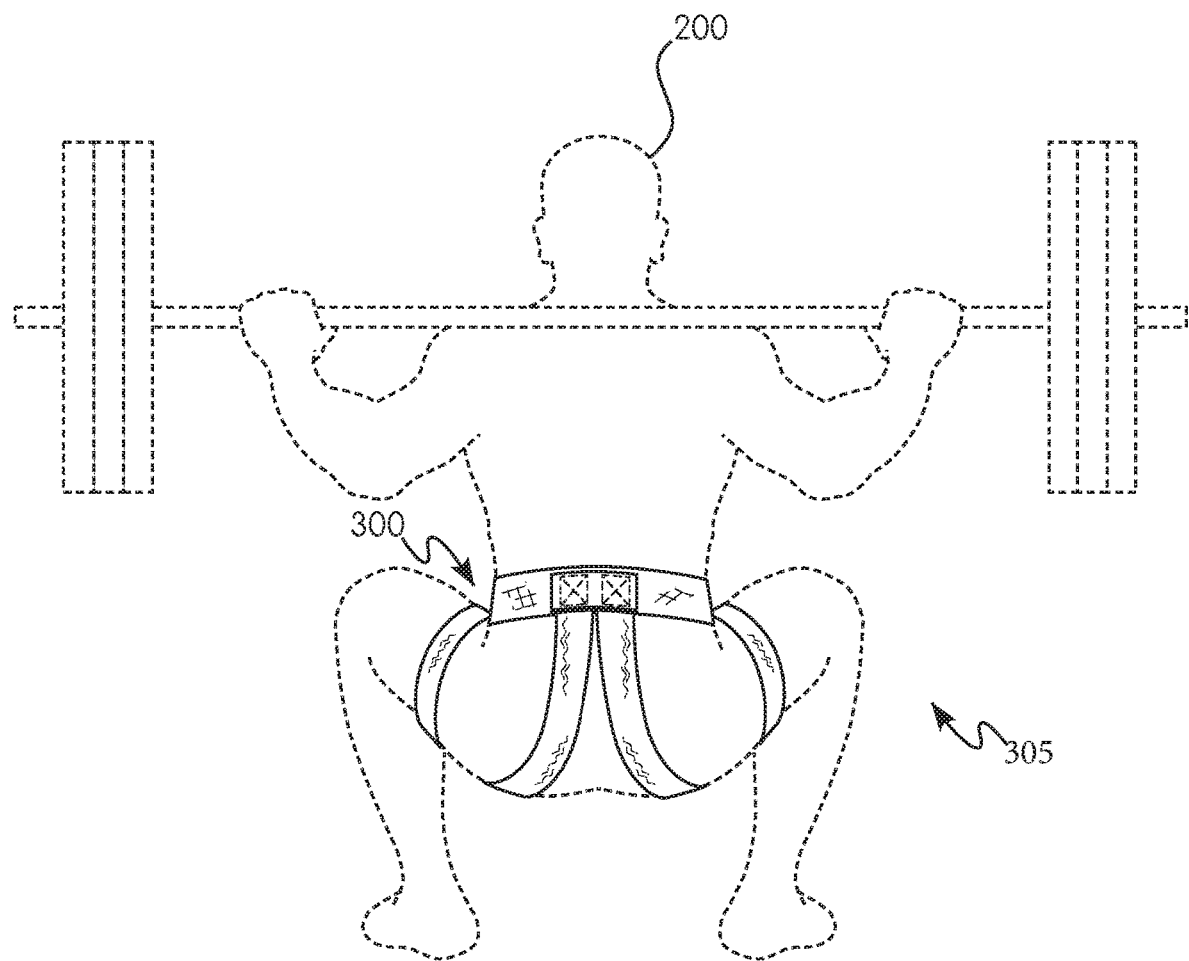
FIG. 9 is a rear perspective view of the user and device shown in FIG. 8 with the user in the bottom position of a squat exercise in accordance with a non-limiting embodiment of the invention.

With reference to FIGS. 8 and 9, FIG. 8 is a rear perspective view of a user in the top position of a squat exercise and wearing device 300 in accordance with a non-limiting embodiment of the present invention, and FIG. 9 is a rear perspective view of the user and device shown in FIG. 8, with the user in the bottom position of a squat exercise in accordance with a non-limiting embodiment of the invention.

In the non-limiting embodiment shown in FIGS. 8 and 9, the device 300 is strapped around a user's waist and thighs such that the biasing straps are positioned medially of the positioning shown in FIGS. 4 and 5. With reference to FIG. 9, as the user 200 "sits" into the lower position 305 of a squat exercise, each biasing strap stretches across its respective buttock and rear upper thigh and imparts a biasing force which urges the user back towards the upper position 303. In this way, the device 300 supplements a user's natural strength and reduces fatigue of the joints (e.g., the knees) and smaller muscles of the lower body. In particular, it is noted that due to the positioning and elastic characteristics of the biasing straps, the biasing forces exerted on the user increase as the user moves toward the lower position 305 of the exercise, which is often where a user experiences the most difficulty in the performance of a squat or similar compound weightlifting exercise, and decreases as the user moves back toward the upper position 303, which is often the least strenuous portion of the exercise. As such, the user may be enabled to perform a squat exercise or other compound exercise with a greater weight or perform more repetitions with the same weight and this may allow the user to strengthen his or her larger muscles by reducing the extent the user is limited by weaknesses in smaller muscles and joints or by the increased difficulty of the exercise near the lower position 305 thereof. Further, this may allow the user to provide further exercise to various muscles that are primarily used in an isometric fashion during a squat exercise or other compound exercise, while reducing the extent to which the user is limited by lower body muscles which move to a greater extent during the exercise (e.g., the quadriceps, hamstrings, and glutes).

Although FIGS. 8 and 9 illustrate the function of a non-limiting embodiment of the invention during a squat exercise, as noted above, non-limiting embodiments of the present invention may also be utilized in a similar way for other compound exercises that focus at least partially on the lower body.

Figure 10:
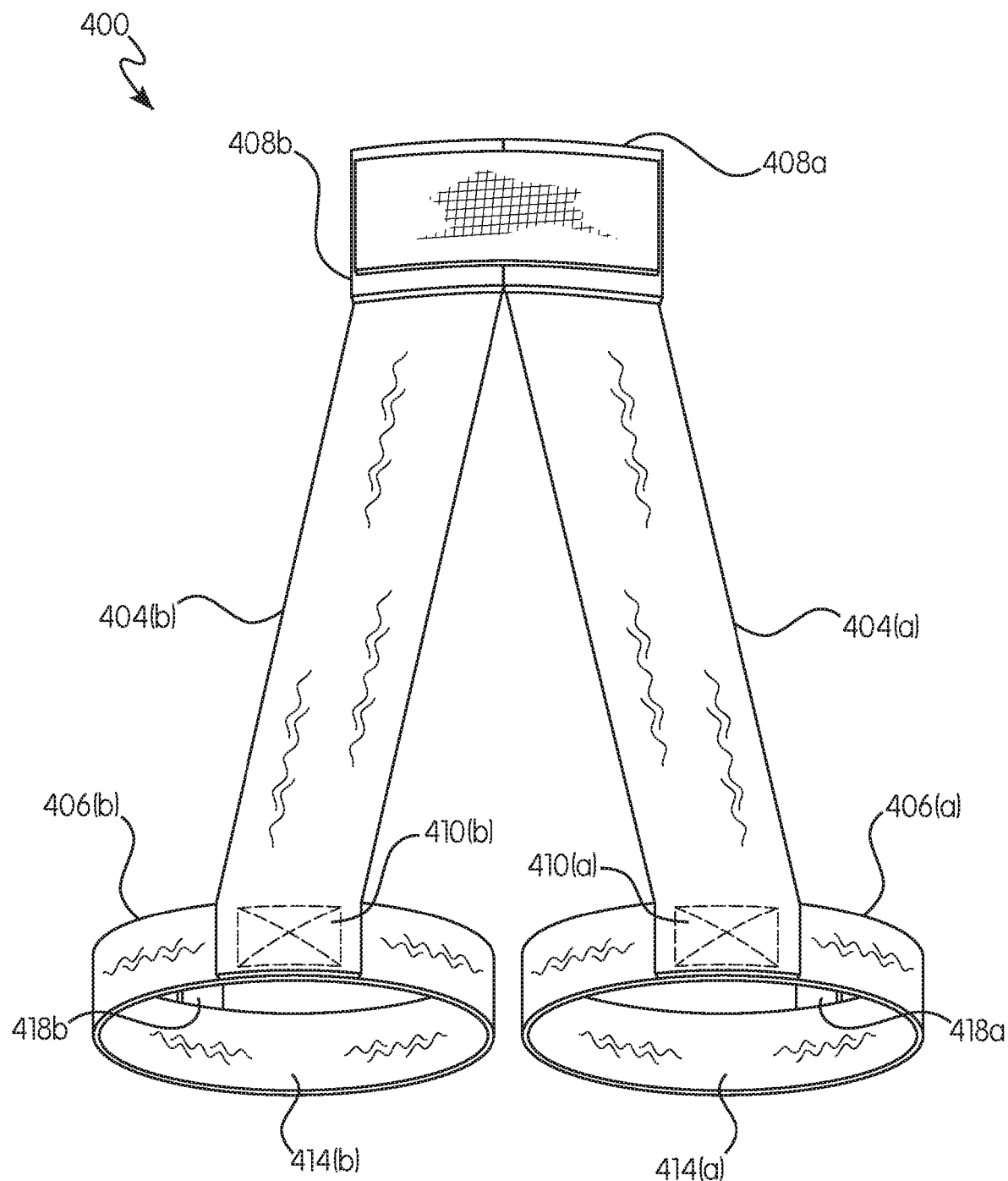
FIG. 10 is a rear perspective view of a device for reinforcing the lower body during a compound weightlifting exercise in accordance with a non-limiting embodiment of the present invention.
Figure 11:
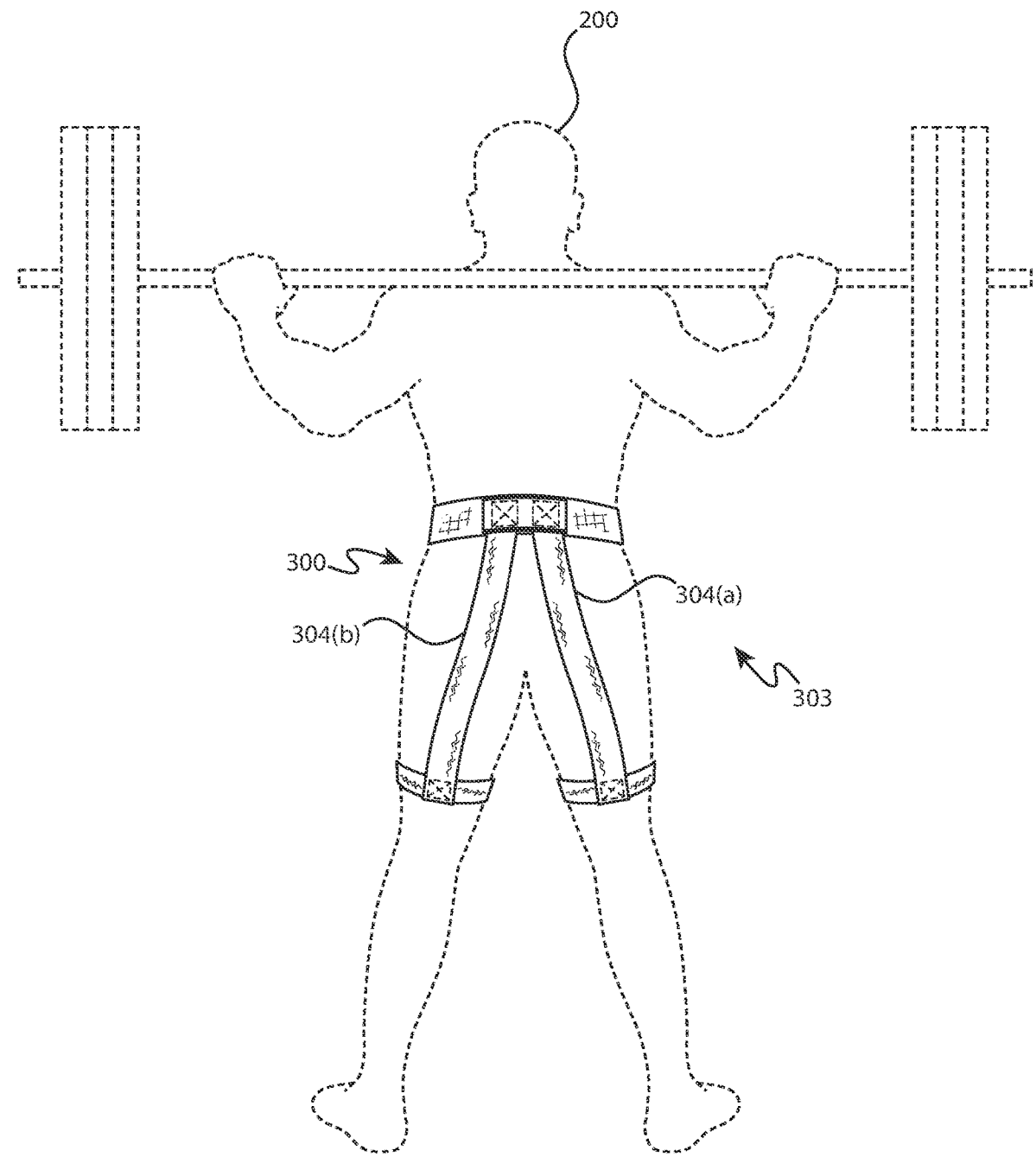
FIG. 11 is a rear perspective view of a user in the top position of a squat exercise while wearing a device for reinforcing the lower body during a compound weightlifting exercise in accordance with a non-limiting embodiment of the present invention.

Referring now to FIG. 10, shown is a non-limiting embodiment of the invention where a waistband is not included. In this way, the device 400 can be attached to a user's weight belt. Device 400 continues to include two biasing straps 404(a, b), the upper ends of which are attached to a posterior portion of the device 400 at connection points 408(a, b). In the non-limiting embodiment shown, the waistband connection points 408(a, b) are not substantially separated (as compared to the non-limiting embodiment of FIGS. 1 and 2), such that the connection points can be considered to be the same connection point. The non-limiting embodiment shown in FIG. 10 lacks a waistband, but connection points 408(a, b) may be provided on a loop or other arrangement of material that allows a weight belt (not shown) to be passed therethrough, securing the device 400 to the weight belt.

With continuing reference to FIG. 10, as in other non-limiting embodiments, the lower end of each biasing strap 404(a, b) is attached to a posterior portion of a respective thigh band 406(a, b) at a thigh band connection point 410(a, b), with the respective thigh band connection points 410(a, b) falling approximately in the middle of the back of the thigh when the device 400 is worn. Each thigh band 406(a, b) is configured to fit around a user's thigh. In the non-limiting embodiment shown in FIG. 10, unlike that shown in FIGS. 1 and 2, there is no thigh band closure. Rather, in the non-limiting embodiment shown in FIG. 10, the thigh bands 406(a, b) are continuous loops formed from an elastic material such that they may be slid over the thighs and held in place via elastic forces and friction. As described above with regard to the non-limiting embodiment of FIGS. 1 and 2, it will be appreciated that various configurations are possible in accordance with the present invention.

Further to the above, and with continuing reference to FIG. 10, the non-limiting embodiment shown therein includes tabs 418(a, b) to aid a user in sliding the thigh bands 406(a, b) onto their thighs. Tabs 418(a, b) may be removably secured to thigh bands 406(a, b), or, in non-limiting embodiments, may be formed integrally with the thigh bands 406(a, b), to increase the pressure that can be applied to pull the thigh bands 406(a, b) onto a user's thigh without risking detachment of the tabs therefrom.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A device for reinforcing the lower body during the performance of a compound weightlifting exercise, comprising:
a first thigh band and a second thigh band, each thigh band comprising a continuous loop without a closure and defining an opening for a wearer's thigh;
a first biasing strap and a second biasing strap, each biasing strap having a proximal end and a distal end, the distal end of the first biasing strap and the distal end of the second biasing strap non-releasably connected to the first thigh band and the second thigh band, respectively; and
a waist portion connected to the proximal end of each biasing strap, wherein the waist portion comprises a loop configured to permit a weight belt to pass therethrough,
wherein, when worn, each of the biasing straps extends between the waist portion and the thigh bands such that the first biasing strap extends over the wearer's right buttock and a rear portion of the wearer's right thigh and the second biasing strap extends over the wearer's left buttock and a rear portion of the wearer's left thigh, and wherein the thigh bands are positioned on the wearer's thighs.

2. The device of claim 1, wherein the thigh bands are formed of a material having a lower linear elasticity than a material forming the biasing straps.

3. The device of claim 1, wherein the thigh bands are formed of a material that stretches linearly by no more than 15% when exposed to 50 pounds of tension.

4. The device of claim 1, wherein, when worn, the thigh bands are positioned around each of the wearer's thighs closer to a knee of the wearer than a groin of the wearer.

5. The device of claim 1, wherein the thigh bands are formed of a material that stretches linearly by approximately 50% when exposed to 50 pounds of tension.

6. The device of claim 1, wherein the biasing straps are formed of a material that stretches linearly by approximately 75% of its non-stressed length when exposed to 50 pounds of tension.

7. A method of reinforcing a wearer's lower body during the performance of a compound weightlifting exercise, comprising:
positioning the device of claim 1 on a wearer, such that:
the thigh bands are positioned around each of the wearer's thighs;
the waist portion is positioned at the wearer's waist; and
the first biasing strap extends over the wearer's right buttock and rear portion of the wearer's right thigh and the second biasing strap extends over the wearer's left buttock and rear portion of the wearer's left thigh.

8. The method of claim 7, wherein the thigh bands are positioned closer to a knee of the wearer than a groin of the wearer.

9. The method of claim 7, wherein, when the wearer is in an extended position of the compound weightlifting exercise wherein the wearer's legs are approximately straight, the biasing straps are in a first, unstressed state.

10. The method of claim 7, wherein, as the wearer bends the wearer's knees during performance of the compound weightlifting exercise, the waist portion and the thigh bands exert tension on the biasing straps, causing the biasing straps to stretch over the wearer's buttocks and a rear portion of the wearer's thighs such that a biasing force is exerted on the wearer, which urges the wearer back toward the extended position.

11. The method of claim 7, wherein the thigh bands are formed of a material that stretches linearly by approximately 50% when exposed to 50 pounds of tension.

12. The method of claim 7, wherein the biasing straps are formed of a material that stretches linearly by approximately 75% of its non-stressed length when exposed to 50 pounds of tension.

13. The method of claim 7, wherein the compound weightlifting exercise is selected from the group consisting of barbell squat, barbell front squat, body-weight squat, conventional deadlift, sumo deadlift, Romanian deadlift, and leg press.

14. The device of claim 1, wherein each thigh band comprises a tab configured to permit the wearer to pull the thigh band onto their thigh.

15. A device for reinforcing the lower body during the performance of a compound weightlifting exercise, consisting of:
   a first thigh band and a second thigh band, each thigh band consisting of a continuous loop without a closure and defining an opening for a wearer's thigh, each thigh band configured to be positioned above the wearer's knee, each thigh band optionally having a tab configured to permit the wearer to pull the thigh band onto their thigh;
   a first biasing strap and a second biasing strap, each biasing strap consisting of a proximal end and a distal end, the distal end of the first biasing strap and the distal end of the second biasing strap non-releasably connected to the first thigh band and the second thigh band, respectively; and
   a waist portion connected to the proximal end of each biasing strap, wherein the waist portion consists of a loop configured to permit a weight belt to pass therethrough,
   wherein, when worn, each biasing strap extends between the waist portion and the respective thigh band, over one of the wearer's buttocks and a rear portion of the wearer's thigh, such that the thigh bands are positioned on the wearer's thigh, and
   wherein the first biasing strap and second biasing strap are configured such that, when worn, the first biasing strap and the second biasing strap do not cross.

* * * * *